United States Patent [19]

Majoie et al.

[11] Patent Number: 4,680,402
[45] Date of Patent: Jul. 14, 1987

[54] BENZOYL-PHENYL-PIPERIDINE DERIVATIVES

[75] Inventors: Bernard Majoie, Dijon; Francois Bellamy, Saulon-la-Rue; Pierre Dodey; Jacques Robin, both of Dijon, all of France

[73] Assignee: Societe de Recherches Industrielles (S.O.R.I.), Paris, France

[21] Appl. No.: 868,443

[22] Filed: May 30, 1986

Related U.S. Application Data

[60] Continuation-in-part of Ser. No. 697,160, Feb. 1, 1985, abandoned, which is a division of Ser. No. 391,915, Jun. 24, 1982, Pat. No. 4,528,294.

[30] Foreign Application Priority Data

Jun. 29, 1981 [FR] France .................. 81 12745

[51] Int. Cl.$^4$ .................. C07D 295/10; C07D 211/52; C07D 211/46; C07D 211/14
[52] U.S. Cl. .................. 546/235; 546/217; 546/220; 546/221
[58] Field of Search ................ 546/235, 217, 220, 221

[56] References Cited

U.S. PATENT DOCUMENTS 4,064,121 12/1977 Toth et al. .................. 546/235

OTHER PUBLICATIONS

C. V. T. Campbell et al, Jour. Chem. Soc. (1941), pp. 747–750.

H. Mohrle et al, Arch. Pharm. (Weinheim) (1979), vol. 312, pp. 219–230.
Loudon et al, J. Chem. Soc. (1954), pp. 1134–1137.

Primary Examiner—Norma S. Milestone
Attorney, Agent, or Firm—Schwartz, Jeffery, Schwaab, Mack, Blumenthal & Evans

[57] ABSTRACT

Intermediate products usable in particular for preparing corresponding amino derivatives by converting their nitro function, said products being of formula:

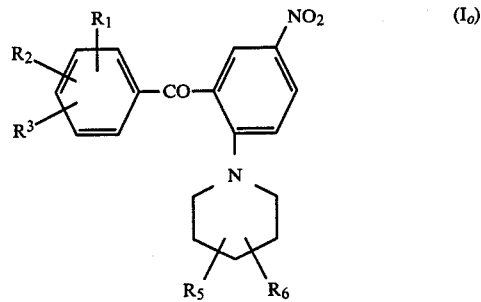

in which:
$R_1$, $R_2$ and $R_3$, which are identical or different, each represent an atom of hydrogen, a halogen, a lower alkyl group or a lower alkoxy group;
$R_5$ and $R_6$, which are identical or different, each represent an atom of hydrogen, a lower alkyl group, an OH group, a phenyl group or a benzyl group.

2 Claims, No Drawings

BENZOYL-PHENYL-PIPERIDINE DERIVATIVES

The present invention is a continuation-in-part application of Ser. No. 697,160, filed Feb. 1, 1985, now abandoned which in turn is a divisional application of Ser. No. 391,915 filed, June 24, 1982, which issued as U.S. Pat. No. 4,528,294 on July 9, 1985.

The present invention relates as new industrial products to derivatives belonging to the family of benzoyl-phenylpiperidines, namely derivatives of 2-piperidinobenzophenone of formula I hereinafter. It also relates to the method for preparing same It is known that a certain number of benzoylphenyl-piperidine derivatives (which do not correspond to formula I hereinafter) has already been described. In particular, French Pat. Nos. 1 375 300 and 1 403 939 disclose the [2-(piperidinyl)phenyl]-2-amino-5-chloro-phenyl)-methanone as intermediate product of synthesis in the preparation of benzodiazepines; French Pat. No. 1 350 325 discloses the [2-amino-5-(1-piperidinyl)-phenyl](phenyl)-methanone and [2-nitro-5-(1-piperidinyl)-phenyl-]-(phenyl)methanone as intermediate products of synthesis in the preparation of benzodiazepines; French Pat. Nos. 74 25070 (publication No. 2 238 480) and 74 25735 (publication No. 2 238 483) disclose the [3-amino-4-(1-piperidinyl)-phenyl]-(phenyl)-methanone and [3-nitro-4-(1-piperidinyl)-phenyl]-(phenyl)-methanone, recommending them as agents inhibiting the hepatic microsomal enzyme and antipyretic agents, and the Article by LOUDON et al., J. Chem. Soc., 1954, pages 1134–1137 discloses [3,5-dinitro-2-(1-piperidinyl)-phenyl]-(phenyl)-methanone.

It has been found that the products of formula:

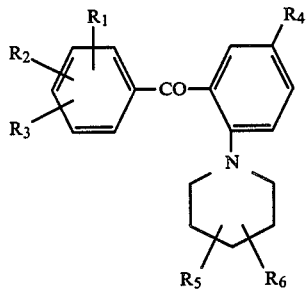

in which :
R₁, R₂ and R₃, which are identical or different, each represent an atom of hydrogen, a hydroxy group, CF₃, a halogen, a lower alkyl group or a lower alkoxy group;
R₄ represents an atom of hydrogen, a halogen, an NO₂ group, an NR'R" group [where R' and R", which are identical or different, represent an atom of hydrogen, a lower alkyl group or a CO₂R group (where R represents a lower alkyl group or a benzyl group)];
R₅ and R₆, which are identical or different, each represent an atom of hydrogen, a lower alkyl group, an OH group, a phenyl group or a benzyl group; and their acid addition salts had particularly advantageous therapeutical properties due to their immunological action.

Lower alkyl and lower alkoxy groups are understood here to mean a branched or straight hydrocarbon radical, containing from 1 to 4 atoms of carbon, such as for example the methyl, ethyl, n-propyl, isopropyl, n-butyl, isobutyl, tertiobutyl groups and the methoxy, ethoxy, n-propoxy, isopropoxy, n-butoxy, isobutyloxy and tertiobutyloxy groups.

Atom of halogen is understood here to mean an atom of chlorine, an atom of bromine or an atom of fluorine.

Acid addition salts are understood here to mean the addition salts obtained by reaction of a free base of formula I with an inorganic or organic acid. From the acids which are appropriate for this purpose, particular mention may be made of the hydrochloric, hydrobromic, sulphuric, phosphoric, acetic, fumaric, maleic, oxalic, citric, tartaric, lactic, malic, benzoic, succinic, phenylacetic, methanesulphonic, ethanesulphonic, paratoluenesulphonic acids.

The compounds of formula I are prepared according to the method consisting in:

(i) reacting a 2-halogeno-5-nitro-benzophenone of formula

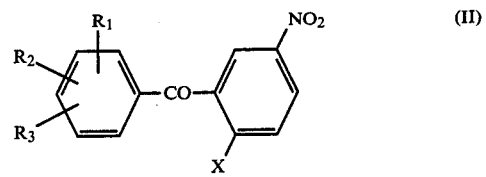

[in which R₁, R₂ and R₃ are defined as hereinabove and X represents an atom of halogen (preferably Cl or F to obtain high yields)], with a possibly substituted piperidine of formula:

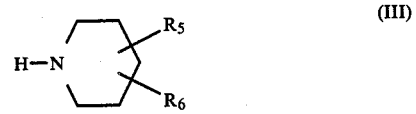

(in which R₅ and R₆ are defined as hereinabove), to obtain a nitro compound of formula

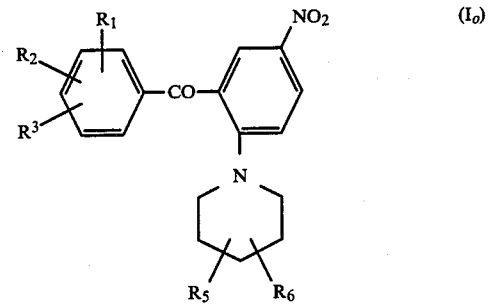

(ii) submitting the compound Io thus obtained to a reduction reaction of the nitro group into amino group to obtain an amino derivative of formula I where R₄=NH₂, then, if need be, submitting said amino derivative to a reaction of deamination, to an alkylation or to a reaction of conversion of the amino group into halogen group.

The reaction of the 2-halogeno-5-nitro-benzophenone II with the piperidine III is carried out in an organic solvent such as hydrocarbons (particularly aromatic hydrocarbons), ethers and alcohols, in the presence of an inorganic or organic base. In practice, one mole of II will be reacted with at least 1.1 mole of III at a temperature of between 15° C. and the reflux temperature of the reaction medium.

The reduction of the nitro group will be conducted in an organic solvent, preferably ethanol, in the presence of iron and concentrated hydrochloric acid (HCl 5N–12N) and at a temperature of between 15° C. and the boiling point of the solvent.

Deamination will be effected by diazotization of the amino group then substitution of the diazonium group by the atom of hydrogen in the presence of copper, at a temperature of between −20° C. and +20° C., and preferably at 0° C.

The diazonium group may also be replaced by an atom of chlorine or an atom of bromine under Sandmeyer's reaction conditions.

An amidification of the amino group will be effected by reaction of a compound of formula (I) where $R_4$=NH$_2$ with an alkyl or benzyl chloroformiate in an organic solvent, preferably an aromatic hydrocarbon, such as for example toluene, in the presence of an inorganic base, such as for example $K_2CO_3$ and at a temperature of between 0° C. and the boiling point of the solvent, and preferably at room temperature (15°–20° C.).

Alkylation of the amino group may be effected by reaction with an alkyl halide or according to Eschweiler-Clark's reaction in the case of a methylation.

It is thus clear that the nitro compounds of formula ($I_o$) are particularly useful intermediate products for preparing the compounds of formula I.

The present invention therefore relates to the products of formula ($I_o$), as intermediate products for use in the preparation, in particular by reduction, of the corresponding amino derivatives:

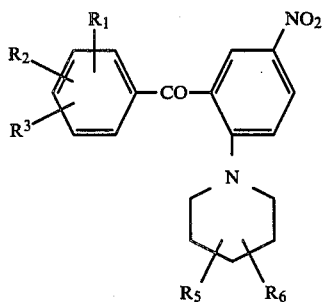

in which $R_1$, $R_2$, $R_3$, $R_5$ and $R_6$ are as defined above.

As indicated hereinabove, the compounds of formula ($I_o$) are prepared by reacting 2-halogeno-5-nitro-benzophenone (II) with piperidine (III), optionally substituted, with an organic solvent; reactions of this type are often recommended in the prior art. Examples 1 to 24 hereafter describe the preparation of various products of Formula $I_o$, using the same technique.

But it has also been found, and this is one aspect of the present invention, that it was particularly advantageous to prepare the products of formula ($I_o$) by reacting a 2-halogeno-5-nitro-benzophenone of formula (II) with an optionally substituted piperidine of formula (III), by operating in an aqueous medium, which contains at least 20 % in volume of water, and which can contain up to 80% in volume of at least one aromatic hydrocarbon, preferably toluene.

It will be noted that the use of an aqueous medium such as described hereinabove to carry out said reaction is nonobvious for two reasons: first the known prior art indicates that this type of reaction must be conducted in a water-free organic medium (or anhydrous organic medium), and second, the starting products are not soluble in aqueous mediums such as used in the present invention, so that the recommended reaction is heterogeneous, yet, despite that heterogeneous character which chemists often try to avoid, the use of such aqueous mediums present considerable advantages:
improvement of the reaction yield,
possibility of energetic gain,
much easier recovery of the formed product.

Examples 25 to 34 illustrate the method according to the invention using as reaction medium, either pure water or a mixture of water and toluene.

Finally, Example 35 illustrates a method for converting a nitro derivative of formula ($I_o$) into a corresponding amino derivative of formula (I) in which $R_4$ is NH$_2$.

EXAMPLE 1

[2-(4-methyl-1-piperidinyl)-5-nitrophenyl]-(4-chlorophenyl)-methanone

A mixture of 0.07 mole (20.7 g) of 2,4'-dichloro-5-nitrobenzophenone, 0.1 mole (11.4 ml) of 4-methylpiperidine and 10 g of $K_2CO_3$ in 100 ml of anhydrous ethanol is heated for 3 hours to reflux. After cooling of the reaction medium, the resulting precipitate is filtered, washed in water, dried then re-crystallized in ethanol. 18 g (yield: 71.7%) of the expected product are thus obtained. M.P. 136° C.

EXAMPLE 2

[2-(4-methyl-1-piperidinyl)-5-nitrophenyl]-(2-chlorophenyl)- methanone

A mixture of 0.012 mole (3.6 g) of 2,2'-dichloro-5-nitrobenzophenone, of 0.018 mole (1.8 g ) of 4-methylpiperidine and of 0.012 mole (1.7 g) of potassium carbonate in 100 cm3 of anhydrous ethanol is heated for 1 hour to reflux.

After cooling of the reaction medium, said medium is hydrolyzed and extracted with ethyl acetate.

The organic phase is washed in slightly acidified water then in water until a neutral pH is obtained, then said phase is dried and evaporated.

5 g of oily product is obtained, which product crystallizes.

After re-crystallization in a mixture of ethanol and hexane 3 g of the expected product are obtained (yield: 50%). M.P. 84° C.

EXAMPLE 3

[2-(1-piperidinyl)-3-nitrophenyl]-(4-chlorophenyl)-methanone

Proceeding as in example 2, with 0.035 mole (10.4 g) of 2,4'-dichloro-5-nitro-benzophenone and 0.07 mole (6 g) of piperidine and 0.035 mole (5 g) of calcium carbonate mixed in ethanol, 11 g (Yield: 97%) of the expected product are obtained after recrystallization in ethanol. M.P.=141° C.

EXAMPLE 4

Code No. SR 1416.

[2-(3-methyl-1-piperidinyl)-5-nitrophenyl]-(4-chlorophenyl)-methanone

Proceeding as in example 2, with 0.035 mole (10.4 g) of 2,4'-dichloro-5-nitro-benzophenone, 0.07 mole (7 cm3) of 3-methylpiperidine and 0.035 mole (5 g) of calcium carbonate mixed in ethanol, 12 g (Yield : 96%) of the expected product are obtained. M.P. 112° C.

EXAMPLE 5

Code No. SR 1417

[2-(4-methyl-1-piperidinyl)-5-nitrophenyl]-(4-methylphenyl)-methanone

Proceeding as in example 2, with 0.045 mole (13 g) of 2-chloro-4'-methyl-5-nitro-benzophenone, 0.1 mole (11.3 cm3) of 4-methyl piperidine and 0.045 mole (6.2 g) of calcium carbonate mixed in ethanol, 14 g (Yield: 95%) of the expected product are obtained. M.P. 86° C.

EXAMPLE 6

Code No. SR 1418

[2-(4-methyl-1-piperidinyl)-5-nitrophenyl]-2,4-dimethylphenyl)methanone

Proceeding as indicated in Example 2, with 0.05 mole (14.5 g) of -chloro-2',4'-dimethylbenzophenone, 0.1 mole (11.3 cm3) of 4-methyl piperidine and 0.05 mole (7 g) of calcium carbonate mixed in ethanol, 17 g (Yield: 94%) of the expected product are obtained. M.P. 88° C.

EXAMPLE 7

Code No. SR 1420

[2-(3,5-dimethyl-1-piperidinyl)-5-nitrophenyl]-(4-chlorophenyl) methanone.

Proceeding as indicated in example 2, with 0.035 mole (10.4 g) of 2,4'-dichloro-5-nitro-benzophenone, 0.07 mole (8 cm3) of 3,5-dimethylpiperidine and 0.035 mole (5 g) of calcium carbonate in ethanol, 12.8 g (Yield: 97%) of the expected product are obtained. M.P 159° C.

EXAMPLE 8

Code No. SR 1425

[2-(2-methyl-1-piperidinyl)-5-nitrophenyl]-(4-chlorophenyl)-methanone

Proceeding as indicated in example 2, from 0.035 mole (10.4 g) of 2,4'-dichloro-5-nitro-benzophenone, 0.07 mole (7 cm3) of 2-methylpiperidine and 0.035 mole (5 g) of calcium carbonate in ethanol, 5.1 g (Yield: 40%) of the expected product are obtained after recrystallization in ethanol. M.P. 142° C.

EXAMPLE 9

Code No. SR 1426

[2-(4-methyl-1-piperidinyl)-5-nitrophenyl]-(4-methoxyphenyl)-methanone

Proceeding as indicated in example 2, with 0.0635 mole (18.5 g) of 2-chloro-4'-methoxy-5-nitro-benzophenone, 0.076 mole (10.5 g) of calcium carbonate and 0.127 mole (12.57 g) of 4-methyl piperidine in 50 cm3 of ethanol, 12.2 g (Yield: 53%) of the expected product are obtained. M.P. 119° C.

EXAMPLE 10

[2-(4-methyl-1-piperidinyl)-5-nitrophenyl]-(phenyl)methanone

Proceeding as indicated in example 2, with 0.03 mole (7.8 g) of 2-chloro-5-nitro-benzophenone, 0.05 mole (5.7 cm3) of 4-methylpiperidine and 0.03 mole (4.1 g) of calcium carbonate in 80 cm3 of ethanol, 8.6 g (Yield: 88%) of the expected product are obtained. M.P. 81° C.

EXAMPLE 11

Code No. SR 1419

[2-(4-methyl-1-piperidinyl)-5-nitrophenyl]-(3,4-dichlorophenyl)methanone.

Proceeding as indicated in example 2, with 0.03 mole (10 g) of 2,3',4'-trichlorobenzophenone, 0.05 mole (5 g) of 4-methyl piperidine and 0.03 mole (4.2 g) of calcium carbonate, 11 g (Yield: 92%) of the expected product are obtained. M.P. 116° C.

EXAMPLE 12

[2-(4-methyl-1-piperidinyl)-5-nitrophenyl]-(4-bromophenyl)-methanone

Proceeding as indicated in example 2, with 0.037 mole (13.2 g) of 4'-bromo-2-chloro-4-nitro-benzophenone, 0.045 mole (6.2 g) of calcium carbonate and 0.075 mole (8.9 cm3) of 4-methyl piperidine in 50 cm3 of ethanol, 7.8 g (Yield: 55%) of the expected product are obtained after re-crystallization in toluene. M.P.: 142° C.

EXAMPLE 13

[2-(4-benzyl-1-piperidinyl)-5-nitrophenyl]-(4-chlorophenyl)-methanone

Proceeding as indicated in example 2, with 3.38 $10^{-3}$ mole (1 g) of 2,4'-5-nitrobenzophenone, 5 $10^{-3}$ mole (0.9 cm3) of 4-benzylpiperidine and 5 $10^{-3}$ mole (0.7 g) of calcium carbonate in 10 cm3 of N,N-dimethyl acetamide, 1.4 g (Yield: 96%) of the expected product are obtained. M.P. 211° C.

EXAMPLE 14

[2-(4-hydroxy-1-piperidinyl)-5-nitrophenyl]-(4-chlorophenyl)-methanone

Proceeding as indicated in example 2, with 0.0506 mole (15 g) of 2,4'-dichloro-5-nitro-benzophenone, 0.076 mole (10.5 g) of calcium carbonate and 0.076 mole (76.8 g) of 4-hydroxypiperidine, in 100 cm3 of ethanol, 12.7 g (Yield: 70%) of the expected product are obtained after re-crystallization in ethyl acetate. M.P. 142° C.

EXAMPLE 15

[2-(4-methyl-1-piperidinyl)-5-nitrophenyl]-(2,4-dichlorophenyl)methanone

Proceeding as indicated in example 2, with 0.053 mole (17.5 g) of 2,2',4'-trichloro-5-nitro-benzophenone, 0.088 mole (8.8 g) of 4-methylpiperidine and 0.0712 mole (9.8 g) of calcium carbonate in 50 cm3 of ethanol, 15.5 g (Yield: 75%) of the expected product are obtained after re-crystallization in a mixture of isopropyl ether and toluene (70 v./30 v.) M.P.: 103° C.

EXAMPLE 16

[2-(4-ethyl-4-methyl-1-piperidinyl)-5-nitrophenyl]-(4-chlorophenyl)methanone

Proceeding as indicated in example 2 with 0.0734 mole (21.7 g) of 2,4'-dichloro-5-nitro-benzophenone, 0.11 mole (18 g) of 4-ethyl4-methylpiperidine and 0.22 mole (30.4 g) of calcium carbonate in 100 cm3 of N,N-dimethyl acetamide, 16.3 g (Yield: 57%) of the expected product are obtained after re-crystallization in isopropyl ether. M.P.: 105° C.

Examples 1 to 16 are re-grouped in Table I; to this table have been added the characteristics of eight other products obtained according to the same method and codified in Examples 17 to 24.

PREPARATION OF 2-(4-methyl-1-piperidinyl)-5-nitro-4'-chlorobenzophenone (a) Reaction with water A mixture of 0.024 mole (0.96 g) of NaOH, 25 ml of water, 0.02 mole (5.92 g) of 2,4'-dichloro-5-nitro-benzophenone and of 0.022 mole (2.6 ml) of 4-methylpiperidine is heated to 80° C. for three and a half hours. After cooling the reaction medium to normal temperature the resulting precipitate is filtered, washed in water and dried giving 6.74 g (Yield: 94%) of the expected product. M.P.=138° C. (Ex. 25) The compounds listed hereunder are obtained by reacting, in the same conditions as above, the 2,4'-dichloro-5-nitro-benzophenone with other piperidine derivatives (2-methyl, 3-methyl, 3,5-dimethylpiperidine):

The 2-(3-methyl-1-piperidinyl)-5-nitro-4'-chlorobenzophenone (Yield: 97%, reaction time: 3 hours)—M.P. 112° C.(Ex. 27).

The 2-(2-methyl-1-piperidinyl)-5-nitro-4'-chlorobenzophenone (Yield: 91%, Reaction time: 24 hours)—M.P. 140° C. (Ex. 31).

The 2-(3,5-dimethyl-1-piperidinyl)-5-nitro-4'-chlorobenzophenone (Yield: 95.8%, Reaction Time: 2 hours). M.P. 160° C. (raw material), M.P. 171° C.(Toluene) (Ex. 30.)

The following compounds are obtained by reacting, in the same conditions, other derivatives of the 2-chloro-5-nitrobenzophenone (2'-chloro, 3'-chloro, 3',4'-dichloro,4'-methyl, 4'-methoxy, 2',4α-dimethyl) with 4-methylpiperidine:

The 2-(4-methyl-1-piperidinyl)-5-nitro-3'-chlorobenzophenone (Yield: 93.4%, Reaction time: 2 hours), M.P. 86° C. (Ex. 34).

The 2-(4-methyl-1-piperidinyl)-5-nitro-4'-methylbenzophenone (Yield: 81%, Reaction time=1 hour 30 mins.), M.P. 110° C. (isopropyl ether)(Ex. 28.)

The 2-(4-methyl-1-piperidinyl)-5-nitro-4'-methoxybenzophenone (Yield: 88.4%, Reaction time: 1 hour), M.P. 100° C. (raw material) M.P. 177° C. (isopropyl ether) (Ex. 32), The 2-(4-methyl-1-piperidinyl)-5-nitro-3',4'-dichlorobenzophenone (Yield: 97%, Reaction time: 9 hours), M.P. 114° C. (Ex. 33).

The 2-(4-methyl-1-piperidinyl)-5-nitro-2',4'-dimethylbenzophenone (Yield: 97.5%, Reaction time: 4 hours), M.P. 106° C. (Ex. 29).

The 2-(4-methyl-1 piperidinyl)-5-nitro-2'-chlorobenzophenone (Yield: 95%, Reaction time: 3 hours), obtained by extraction with ethyl acetate. M.P. 84° C. (washing in isopropyl ether) (Ex. 26).

(b) Reaction with the mixture water-toluene

A mixture of 0.024 mole (0.96 g) of NaOH, 5 ml of water, 15 ml of toluene, 0.02 mole (5.92 g) of 2,4'-dichloro-5-nitro-benzophenone and 0.022 mole (2.6 ml) of 4-methylpiperidine is heated to 80° C. for one hour. After cooling the reaction medium to normal temperature, the resulting precipitate is filtered, washed in water and dried, giving 6.51 g (90.8%) of the expected product. M.P. 138° C. (Ex. 25). By reacting in the same conditions the 2,4'-dichloro-5-nitrobenzophenone with other piperidine derivatives (2-methyl, 3-methyl, 3,5-dimethyl piperidine), the following compounds are obtained:

The 2-(3-methyl-1-piperidinyl)-5-nitro-4'-chlorobenzophenone (Yield: 94.5%, Reaction time: 1 hour 15 mins.) M.P. 111° C. (Ex. 27).

The 2-(2-methyl-1-piperidinyl)-5-nitro-4'-chlorobenzophenone (Yield: 70%, Reaction time: 5 hours) M.P. 140° C. (Ex. 31).

The 2-(3,5-dimethyl-1-piperidinyl)-5-nitro-4'-chlorobenzophenone (Yield: 96.2%, Reaction time: 3 hours). M.P. 164° C. (raw material) M.P. 171° C. (toluene) (Ex. 30).

By reacting in the same conditions, other derivatives of 2-chloro-5-nitro-benzophenone (2'-chloro, 3'-chloro, 3',4'-dichloro, 4'-methyl, 4'-methoxy, 2', 4'-dimethyl) with the 4-methylpiperidine, the following compounds are obtained:

The 2-(4-methyl-1-piperidinyl)-5-nitro-3'-chlorobenzophenone (Yield: 83.6%, Reaction time: one hour 30 mins.), M.P. 88° C. (Ex. 34).

The 2-(4-methyl-1-piperidinyl)-5-nitro-4'-methylbenzophenone (Yield: 97%, Reaction time: 2 hours) M.P. 110° C. (Ex. 28).

The 2-(4-methyl-1-piperidinyl)-5-nitro-4'-methoxybenzophenone (Yield: 68.4%, Reaction time: one hour) obtained by extraction with ethyl acetate. M.P. 120° C. (isopropyl ether) (Ex. 32).

The 2-(4-methyl-1-piperidinyl)-5-nitro-3',4'-dichlorobenzophenone (Yield: 98.3%, Reaction time: 3 hours), M.P. 114° C. (Ex. 33).

The 2-(4-methyl-1-piperidinyl)-5-nitro-2',4'-dimethylbenzophenone (Yield: 88%, Reaction time: 2 hours) M.P. 107° C. (Ex. 29).

The 2-(4-methyl-1-piperidinyl)-5-nitro-2'-chlorobenzophenone (Yield: 95%, Reaction time: 3 hours) obtained by extraction with ethyl acetate, M.P. 84° C. (washed in pentane - isopropyl ether) (Ex. 26).

(c) Reaction in large quantity with the mixture water-toluene

In a reactor of 4-liter capacity, and under mechanical stirring, 50 ml of toluene and 1 kg of 2,4'-dichloro-5-nitrobenzophenone are introduced. Dissolving is partial. Then a solution of 162 g of soda in 500 ml water is added, after what, 368 g (440 ml) of 4-methylpiperidine are dropped through a bromine funnel. The reaction is sufficiently exothermic in large quantity to reach 84° C. in the reactor, so that there is no need to heat at the beginning. At the end of the adjunction, the temperature is kept to 80° C. for about 2 hours until the end of the reaction. The final product crystallizes in situ. About 16 hours after the cooling down of the reaction medium to normal temperature, the resulting crystals are filtered, washed several times in water until a neutral pH is reached, and dried in vacuo at 80° C. to give 1140 g (yield: 94.09%) of the expected product. M.P. 138° C. (Ex. 25).

The results from these tests are given in Table II; it will be noted that in many cases, the same products, obtained in an anhydrous medium on the one hand, and in an aqueous medium according to the invention, on the other hand, have different melting points, it is presumed because hydrates are formed in an aqueous medium.

EXAMPLE 35

This example is solely given to illustrate a method of converting the nitro compound of formula ($I_o$) into a corresponding amino compound of formula (I).

[2-(4-methyl-1-piperidinyl)-5-aminophenyl]-(4-chlorophenyl)-methanol

A mixture of 0.02 mole (7.2 g) of the product obtained in Example 1, 0.2 mole (11.2 g) of powdered iron in 80 ml of the ethanol-water mixture (90:10 v/v and 4 ml of HCl 10N acid is brought to reflux for two hours. After cooling, the reaction medium is filtered, the filtrate is treated with the HCl 10N acid, the solvent is evaporated and the resulting solid product is washed in ethyl acetate, then placed in suspension in the ethyl acetate. Said suspension is treated with sodium bicarbonate and the organic phase is washed in water, then dried and evaporated. 3.9 g of solid product are obtained which, after re-crystallization in hexane, give 2.9 g (yield: 44%) of the expected product. M.P. 89° C.

Analysis

In the NMR spectrum of the product of Example 35 made at 80 MHz in $CDCl_3$, the following chemical displacements are observed (expressed in ppm):

0.70 (intensity=5);
2.50 and 2.80 (intensity=4);
6.80 (intensity=3);
1.37 (intensity=3);
3.58 (intensity=2);
7.35 and 7.70 (intensity=4).

TABLE I

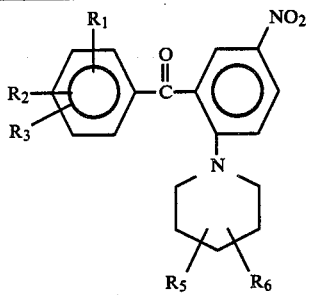

| Ex. n° | $R_1$ | $R_2$ | $R_3$ | $R_5$ | $R_6$ | F°C. |
|---|---|---|---|---|---|---|
| 1 | 4-Cl | —H | —H | 4-$CH_3$ | H | 136 |
| 2 | 2-Cl | —H | H | 4-$CH_3$ | H | 84 |
| 3 | 4-Cl | H | H | H | H | 141 |
| 4 | 4-Cl | H | H | 3-$CH_3$ | H | 112 |
| 5 | 4-$CH_3$ | H | H | 4-$CH_3$ | H | 86 |
| 6 | 2-$CH_3$ | 4-$CH_3$ | H | 4-$CH_3$ | H | 88 |
| 7 | 4-Cl | H | H | 3-$CH_3$ | 5-$CH_3$ | 159 |
| 8 | 4-Cl | H | H | 2-$CH_3$ | H | 142 |
| 9 | 4-$OCH_3$ | H | H | 4-$CH_3$ | H | 119 |
| 10 | H | H | H | 4-$CH_3$ | H | 81 |
| 11 | 3-Cl | 4-Cl | H | 4-$CH_3$ | H | 116 |
| 12 | 4-Br | H | H | 4-$CH_3$ | H | 142 |
| 13 | 4-Cl | H | H | 4-$CH_2$-Ph | H | 211 |

TABLE I-continued

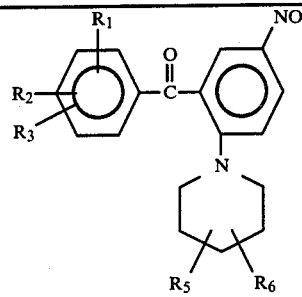

| Ex. n° | $R_1$ | $R_2$ | $R_3$ | $R_5$ | $R_6$ | F°C. |
|---|---|---|---|---|---|---|
| 14 | 4-Cl | —H | —H | 4-OH | H | 142 |
| 15 | 2-Cl | 4-Cl | H | 4-$CH_3$ | H | 103 |
| 16 | 4-Cl | H | H | 4-$CH_3$ | 4-$CH_2CH_3$ | 105 |
| 17 | 4-Cl | H | H | 4-$C(CH_3)_3$ | H | 152 |
| 18 | 4-Cl | H | H | 4-$C_2H_5$ | H | 129 |
| 19 | 4-Cl | H | H | 4n-$C_4H_9$ | H | 105 |
| 20 | 4-Cl | H | H | 4-Ph | H | 167 |
| 21 | 4-Cl | H | H | 4-$CH_3$ | 4-$CH_3$ | 109,5 |
| 22 | 2-Cl | H | H | 4-$C(CH_3)_3$ | H | 171 |
| 23 | 4-Cl | H | H | 4-OH | 4-Ph | 203 |
| 24 | 3-Cl | H | H | 4-$CH_3$ | H | 86 |

TABLE II

| Ex. n° | WATER | | | WATER + TOLUENE | | |
|---|---|---|---|---|---|---|
| | Yield % | M.P. °C. | Time | Yield % | M.P. °C. | Time |
| 25 | 94 | 138 | 3.5 hrs | 94 | 138 | 2.50 hrs |
| 26 | 95 | 84 | 3 hrs | 95 | 84 | 3 hrs |
| 27 | 97 | 112 | 3 hrs | 94.5 | 111 | 1.25 hrs |
| 28 | 81 | 110 | 1.5 hrs | 97 | 110 | 2 hrs |
| 29 | 97.5 | 106 | 4 hrs | 88 | 107 | 2 hrs |
| 30 | 95.8 | 171 | 2 hrs | 96.2 | 171 | 2 hrs |
| 31 | 91 | 140 | 24 hrs | 30 | 140 | 5 hrs |
| 32 | 88.4 | 117 | 1 hrs | 98.4 | 120 | 1 hrs |
| 33 | 97 | 114 | 9 hrs | 98.3 | 114 | 3 hrs |
| 34 | 93.4 | 86 | 2 hrs | 83.6 | 88 | 1.50 hrs |

What we claim is:

1. A compound corresponding to the formula:

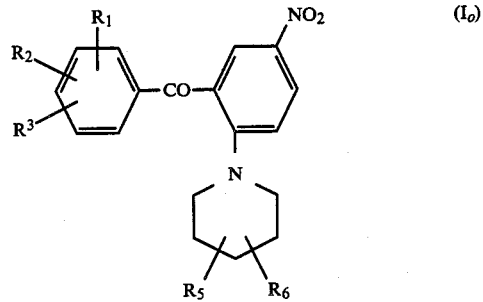

(I$_o$)

in which:

$R_1$ and $R_2$, which are identical or different, each represent an atom of hydrogen, a halogen, a lower alkyl group or a lower alkoxy group;

$R_3$ represents an atom of hydrogen;

$R_5$ and $R_6$, which are identical or different, each represent an atom of hydrogen, a lower alkyl group, an OH group, a phenyl group or a benzyl group, and wherein at least one of $R_1$, $R_2$, $R_5$ and $R_6$ is other than hydrogen.

2. 2-(4-methyl-1-piperidinyl)-5-nitro-4'-chloro-benzophenone.

* * * * *